(12) United States Patent
Thompson et al.

(10) Patent No.: US 6,195,164 B1
(45) Date of Patent: Feb. 27, 2001

(54) SYSTEMS AND METHODS FOR CALIBRATING LASER ABLATIONS

(75) Inventors: Angelina Thompson, San Jose; Terrance N. Clapham, Saratoga; George Caudle, San Jose, all of CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

(21) Appl. No.: 09/187,058

(22) Filed: Nov. 5, 1998

Related U.S. Application Data
(60) Provisional application No. 60/064,724, filed on Nov. 6, 1997.

(51) Int. Cl.[7] .............................. B23K 26/00; G01B 9/00; G01B 11/24
(52) U.S. Cl. .................... 356/376; 356/124; 219/121.6
(58) Field of Search ............................... 250/559.2, 552; 219/121.6; 356/124, 376

(56) References Cited

U.S. PATENT DOCUMENTS

| | | | |
|---|---|---|---|
| 3,912,395 | 10/1975 | Voggenthaler | 356/124 |
| 4,199,816 | 4/1980 | Humphrey | 364/571 |
| 4,410,268 | 10/1983 | Tamaki | 356/124 |
| 5,307,141 | * 4/1994 | Fujieda | 356/124 |
| 5,331,394 | 7/1994 | Shalon et al. | 356/124 |
| 5,350,374 | 9/1994 | Smith | 606/5 |
| 5,406,375 | 4/1995 | Brandstetter | 356/124 |
| 5,464,960 | * 11/1995 | Hall et al. | 219/121.6 |
| 5,624,326 | 4/1997 | Nakamura | 606/12 |
| 5,772,656 | 6/1998 | Klopotek | 606/12 |

OTHER PUBLICATIONS

Stein et al., "Technical operation of the excimer laser" (1997) *The Excimer. Fundamental and Clinical Use*, Slack Inc., publishers, Chapter 7, pp. 63–68.

\* cited by examiner

*Primary Examiner*—Frank G. Font
*Assistant Examiner*—Armando Rodriguez
(74) *Attorney, Agent, or Firm*—Townsend Townsend & Crew LLP; Mark D. Barrish, Esq.

(57) ABSTRACT

Improved systems, methods, and apparatus for calibrating a laser ablation system by measuring the optical power and shape of a test surface that has been ablated by energy delivered from a laser. The quality of the ablated test surface can be monitored to minimize undesirable laser system performance, such as might result from flawed internal optics, misalignment, poor laser fluence and the like. Calibration accuracy is generally enhanced by analyzing distortions of a geometrical pattern superimposed with the ablation test surface. The interaction of the pattern and the lens can be analyzed using a microscope, video camera connector, and other existing components of the laser ablation system, and can also provide quantitative test surface characteristics which may be used to accurately adjust the laser system.

18 Claims, 11 Drawing Sheets

SYSTEMS AND METHODS FOR CALIBRATING LASER ABLATIONS

CROSS-REFERENCES TO RELATED APPLICATIONS

This application is a continuation-in-part of, and claims the benefit of priority from, U.S. Provisional Patent Application Ser. No. 60/064,724, filed Nov. 6, 1997, the full disclosure of which is incorporated herein by reference.

BACKGROUND OF THE INVENTION

The present invention is directed to systems, methods, and apparatus for calibrating laser ablation systems. In particular, the invention relates to methods and apparatus for measuring the refractive power, shape and quality of a laser test ablation on a test surface. The present invention is particularly useful for calibrating excimer lasers used during laser ablation procedures of the eye, such as photorefractive keratotomy (PRK), phototherapeutic keratectomy (PTK), laser in situ keratomileusis (LASIK), or the like.

Ultraviolet and infrared laser based systems and methods are known for enabling ophthalmological surgery on the external surface of the cornea in order to correct vision defects. These procedures generally employ an ultraviolet or infrared laser to remove a microscopic layer of an anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without substantially heating the remaining substrate; the mechanism of the ablation is photochemical, i.e. the direct breaking of intermolecular bonds. The ablation penetrates into the stroma of the cornea to change its contour for various purposes, such as correcting myopia, hyperopia, and astigmatism.

In such laser based systems and methods, the irradiated flux density and exposure time of the cornea to the laser radiation are controlled so as to provide a surface sculpting of the cornea to achieve a desired ultimate surface change in the cornea. To that end, ablation algorithms have been developed that determine the approximate energy density that must be applied to remove a certain depth of tissue from the cornea. At ultraviolet wavelengths, for example, a cumulative energy density of about 1 joule/cm2 will typically ablate corneal tissue to a depth of about one micron when applied in a series of pulses of about 100 to 400 millijoules/cm2. Accordingly, the ablation algorithms are tailored for each procedure depending on the amount and the shape of corneal tissue which will be removed to correct a particular individual's refractive error.

In order to properly use these laser ablation algorithms, the laser ablation system typically should be calibrated. Calibration of the laser system helps ensure removal of the intended shape and quantity of the corneal tissue so as to provide the desired shape and refractive power modification to the patient's cornea. In addition, it is usually desirable to test for acceptable levels of system performance. For example, such tests can help ensure that internal optics are aligned, that laser fluence is accurate, etc.

Ablations of plastic test materials are often performed prior to excimer laser surgery to calibrate the energy density and ablation shape of the laser. During these tests, a lens is ablated into the test plastic, and the refractive power of the test lens is read by a standard lensometer. The reading from the lensometer is then entered back into the laser system so that the system can make appropriate calibration adjustments. The test lens may also be visually evaluated under a magnifying glass or with the microscope of the laser system, and test samples are sometimes sent to a laboratory for accurate evaluation to help determine beam homogeneity and quality.

Although known laser ablation calibration techniques are fairly effective, these methods still suffer from certain disadvantages. For example, delaying each surgery while obtaining accurate laboratory evaluations of a test lens may be impractical. On the other hand, requiring specialized test lens evaluation equipment at each site could add significantly to equipment costs and overall system complexity. Nonetheless, some information beyond refractive power and a visual evaluation of the test lens would be helpful to improve the accuracy of regular calibrations, whether they are performed monthly, daily, or before each ablation procedure.

In light of the above, it would be desirable to provide improved systems, methods, and apparatus for calibrating laser ablation procedures. It would be particularly desirable if such improvements enhanced calibration accuracy without significantly increasing the overall system costs and complexity. It would further be desirable if such improvements could provide quantifiable data which might be used in an automated calibration feedback and adjustment system.

SUMMARY OF THE INVENTION

The present invention is directed to improved systems, methods, and apparatus for calibrating a laser ablation system, such as an excimer laser system for selectively ablating the cornea of a patient's eye. The present invention provides apparatus and methods for measuring the shape of a test surface that has been ablated by energy delivered from a laser, such as an excimer laser. In addition, the present invention provides apparatus and methods for monitoring the quality of the ablated test surface to minimize undesirable system performance, such as flawed internal optics, misalignment, poor laser fluence and the like. Calibration accuracy is generally enhanced by analyzing distortions of a geometrical pattern projected onto and/or viewed through the ablation test surface. Conveniently, the interaction of the pattern and the lens can be analyzed using existing components of the laser ablation system such as a microscope, video camera, computer processor, and other system components. These improved calibration techniques allow enhanced quantitative evaluations of the test surface at low cost and with little delay, and can also be used to accurately and automatically adjust the laser system.

In one aspect, a method is provided for calibrating a laser ablation system. The method includes the steps of selectively ablating a test surface with the laser, superimposing a geometrical test pattern and the ablated test surface to generate a resulting pattern, digitizing at least a portion of the resulting patterns and analyzing the digitized pattern to determine the ablation characteristics of the laser ablation system. The geometric pattern will usually include a plurality of uniformly spaced elements, such as lines, dots, circles, or the like. The test surface is often ablated into a lens that will refract the geometric elements viewed through the lens such that the resulting pattern will provide information regarding the refractive power, shape and quality of the test surface. Advantageously, the effects of the lens on the geometrical pattern may be quantified. Further, by using the digitized images and the laser system computer, adjustments to the laser ablation may be made based on the quantitative measurements of the surface.

Preferably, the test pattern will include a peripheral portion that is disposed around the ablated test surface, and which is not refracted by the test surface. An inner portion is aligned with the test surface and is refracted. The spacing between the geometrical elements can be compared to determine the distribution of refractive power of the test surface, and geometrical elements which extend between the peripheral and inner portions will indicate a contour and quality of the ablation near its edge. If desired, the refractive power may be determined by comparing the ratios of the spacing of the geometrical elements in the center to those at the periphery.

The test surface will typically include a lens, the lens generally comprising a polymer material that can be ablated with an excimer laser in a repeatable, predictable manner. Suitable test ablation materials include polymethylmethacrylate ("PMMA"), VISX calibration media (available from VISX, Incorporated), and the like. The plastic is ablated into a lens having a distribution of refractive power and a particular shape. Typically, the plastic lens will be ablated with approximately the same treatment that will be applied to a patient's cornea. The spacing of the elements in the peripheral and inner portions of the geometrical test pattern can be analyzed to determine the distribution of refractive power of the lens. In addition, the regularity of the lens contour can be measured by determining the parallelism or regularity of the spaced elements.

In a specific configuration, the geometrical test pattern is a reflective surface having a plurality of non-refractive regularly spaced lines. The regularly spaced lines are preferably parallel to each other, and may be horizontal, vertical, concentric circles or a matrix or grid pattern. The parallel line pattern is projected through the ablated lens such that the lines or image can be viewed through, for example, an operating microscope and/or imaged onto a light detector. The line pattern image may then be digitized and analyzed to determine the optical power and shape of the ablated lens.

The present invention also provides a laser calibration system for use with a laser ablation system. The laser ablation system is capable of reshaping a surface by selective laser ablation. The calibration system comprises a selectively laser ablatable test surface and a light projecting assembly. The light projecting assembly projects a geometrical test pattern through the ablated test surface. An imaging assembly is coupled to the light projecting assembly for generating an image of the geometrical test pattern through the ablated test surface to an image analyzer, which determines a contour of the test surface.

In a specific configuration, the light projecting assembly includes a light source and an optical train for directing light from the light source through the ablation test surface. A reference structure is preferably disposed between the light source and the test surface along the optical train. The optical train may further include a light detector positioned to receive light from the test surface to transform the received light into electrical signals. The laser calibration system may further include a processor which analyses the electrical signals to determine the quality, optical power, size, and other characteristics of the test surface to allow adjustments to the laser system.

DESCRIPTION OF THE SPECIFIC EMBODIMENTS

Figure 1:
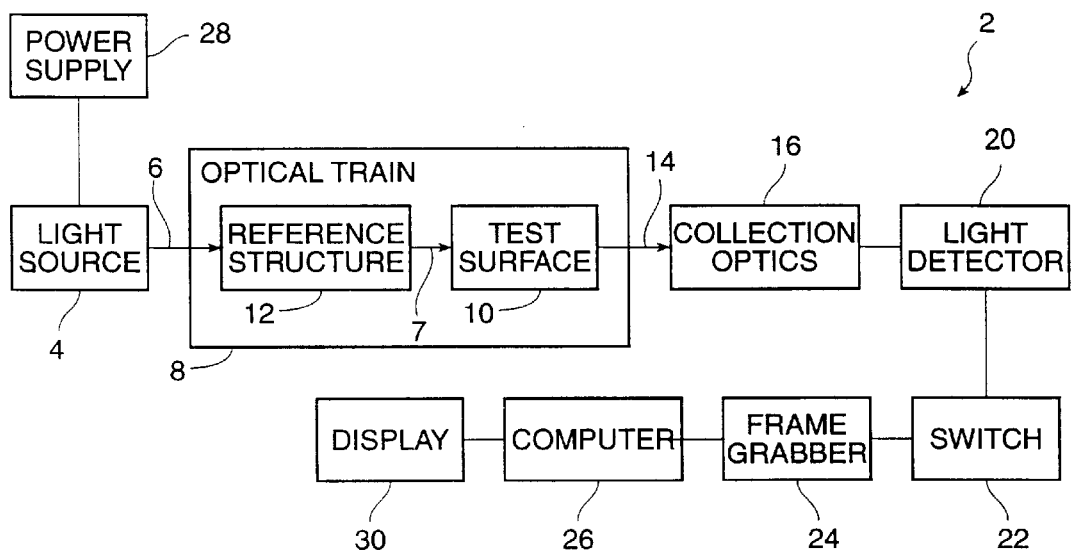
FIGS. 1 and 1A are simplified block diagrams illustrating the functional relationships of optical, mechanical, and electrical components of a calibration system of the present invention.

Referring to FIG. 1, a calibration system 2 for calibrating a laser ablation system is schematically illustrated according to the present invention. Calibration system 2 measures the optical power and shape of a test surface 10 that has been ablated by energy delivered from a laser, such as an excimer laser. FIGS. 2–5 illustrate a calibration card viewer 100 for monitoring the quality (discussed below) of the ablated test surface 10 according to the present invention. Calibration system 2 and calibration card viewer 100 are particularly useful for calibrating a laser ablation system of the type used to ablate a region of the cornea in a surgical procedure, such as excimer laser used in photorefractive keratometry (PRK), phototherapeutic keratectomy (PTK), laser in situ keratomileusis (LASIK) or the like.

Figure 1A:
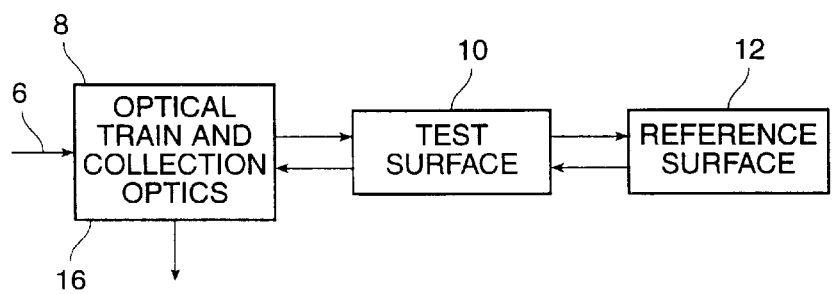

Referring again to FIG. 1, calibration system 2 generally includes a light source 4 for directing a plurality of light rays 6 through an optical train 8. Light source 4 directs the light rays 6 through reference structure 12, which creates a viewable geometrical pattern 7. Light rays from geometrical pattern 7 will pass through test surface 10, which will typically at least partially refract the pattern to produce a resulting patterns 14. Resulting pattern 14 is imaged with collection optics 16 (which may or may not include at least some of the same optics as optical train 8) onto light detector 20 as a measurable optical image. If desired, apertures may be used to increase the depth of field of the images formed by collection optics 16. Also, lenses of varying optical power (not shown) may be inserted into optical train 8 to enhance the images formed by collection optics 16. Optionally, reference structure 12 can comprise a patterned reflective element which reflects light from optical train 8 back through test surface 10, as illustrated in FIG. 1A.

A signal switch 22, a frame grabber 24, and a computer 26 are in electrical communication with the photodetector 20 for digitizing the video images and processing these images for determining the optical power and shape of the test surface 10. Alternatively, resulting pattern 14 may be visually evaluated through collection optics 16, which may comprise a microscope of the laser ablation system, optionally used in combination with the video display for the laser ablation system.

The light source 4 is activated by a power supply 28 to pass light rays 6 through optical train 8, which may include a condenser lens (not shown). Alternatively, the light source 4 may simply illuminate reference structure 12 without requiring additional lenses. Light source 4 may comprise one or more light sources, such as halogen light sources, light emitting diodes, fiberoptics, and the like.

The test surface 10 or calibration card will preferably comprise a material that can be ablated in a repeatable, predictable manner with a laser, such as an excimer laser. In one embodiment, test surface 10 is a sheet of plastic that is ablated into a lens having a refractive power and a shape. Alternatively, test surface 10 may be ablated to define a substantially flat recess.

Figure 5:
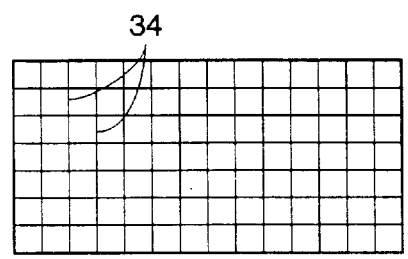
Figure 6:
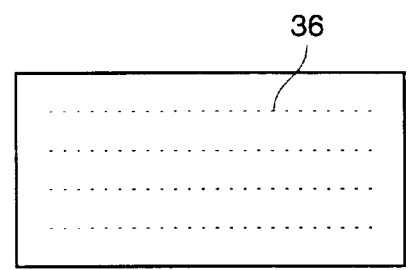
FIGS. 6 and 7 illustrate alternative embodiments of patterned elements according to the present invention.
Figure 7:
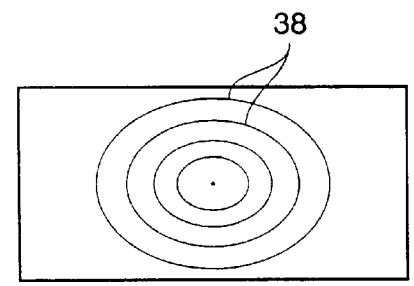
Figure 8A:
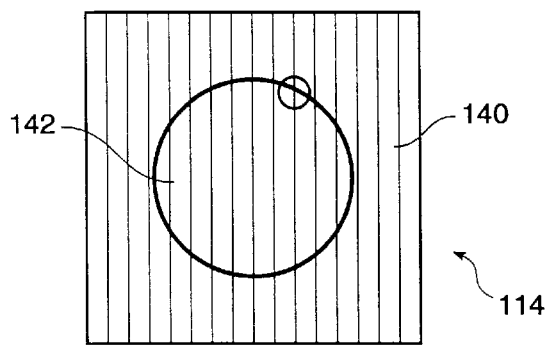
FIGS. 8a, 8b, 8c, 8d, 8e, 9a, 9b, 9c, 9d, 10a, 10b, 10c, 10d and 10e illustrate images demonstrating different line patterns that can be obtained with the system.
Figure 8B:
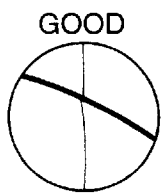
Figure 8C:
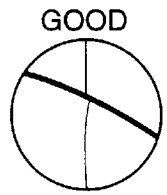
Figure 8D:
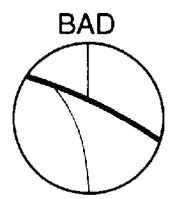
Figure 8E:
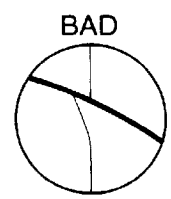

Reference structure 12 for use with calibration system 2 preferably comprises a diffuse surface that minimizes non-uniform light scattering. The diffuse surface will include a plurality of regularly spaced non-reflective elements for generating the image (discussed below). In one embodiment shown in FIG. 4, the non-reflective elements comprise parallel lines 32, which may be horizontal or vertical. Alternatively, the parallel lines may form a grid 34, with both horizontal and vertical lines as shown in FIG. 5. In addition, it should be understood that a variety of other configurations are possible. As shown in FIG. 6, the regularly spaced elements may be dots 36, or they may comprise concentric circles 38 as shown in FIG. 7.

Electrical output signals generated by photodetector 20 are directed by signal switch 22 to a frame grabber 24 which produces a time sequence series of electrical signals representative of the image formed by the collection optics 16. These electrical signals can be displayed as a real time video image in a display apparatus 30. Alternatively or in addition, the electrical signals can be stored in digital form by frame grabber 24 for further analysis by computer 26 and/or supplied to display apparatus 30. Computer 26 will include a processor and appropriate software for calculating the refractive power and the shape of the ablated test surface (discussed below).

Photodetector 20 may comprise a conventional photodetecting device having photocathodes and a video contact image. Alternatively, photodetector 20 may comprise an array of discrete detectors such as a charge couple device (CCD). Typically, the detector will comprise a CCD array with usable aperture dimensions of about 4.8 by 6.0 mm and a resolution of less than about 0.01 mm, and would be sensitive to the light emitted by light source 4. Many suitable photodetectors are commercially available, such as the Electrum EDC 1000U (Electrum Corporation, Princeton, N.J.). The width and spacing between the lines 32 on reflector element 12 will typically depend on the resolution of photodetector 20. In a specific embodiment, the lines are approximately 20 to 100 μm wide, preferably about 50 μm wide, with a spacing of approximately 200 to 1,000 μm from center to center, preferably about 500 μm from center to center.

In use with the present invention, test surface 10 is selectively ablated by delivering energy from a laser (not shown) to form a pre-programmed shape onto test surface 10. The laser ablation system is configured to deliver the appropriate radiation in accordance with the calculated beam delivery parameters for the specific procedure, e.g., the power level and desired shape on the corneal surface. The radiation may be delivered in a single continuous treatment, or in a series of treatments. The laser selected for use preferably emits in the ultraviolet, namely at wavelengths of less than substantially 400.0 nm.

For convenience, the method will be described as applied to a laser photo ablation method (PRK) using an argon fluoride excimer laser which generates ultraviolet radiation at 193.0 nm at predetermined pulse energy densities and repetition rates. In an exemplary embodiment, a VISX STAR Excimer Laser System™ may be used for the ablation (commercially available from VISX, Incorporated of Santa Clara, Calif.). This system produces an output of 193.0 nm, operates at a frequency of 6.0 Hz and is adjusted to deliver uniform fluence of 160.0 millijoules/cm2 with a 6.0 mm diameter ablation zone. Other laser systems suitable for use with the present invention are the T-PRK™ scanning and tracking laser from Autonomous Technologies Corporation, the SVS Apex™ laser from Summit Technology Inc., the Keracor™ 117 scanning laser system from Chiron Vision, or the like.

Figure 2A:
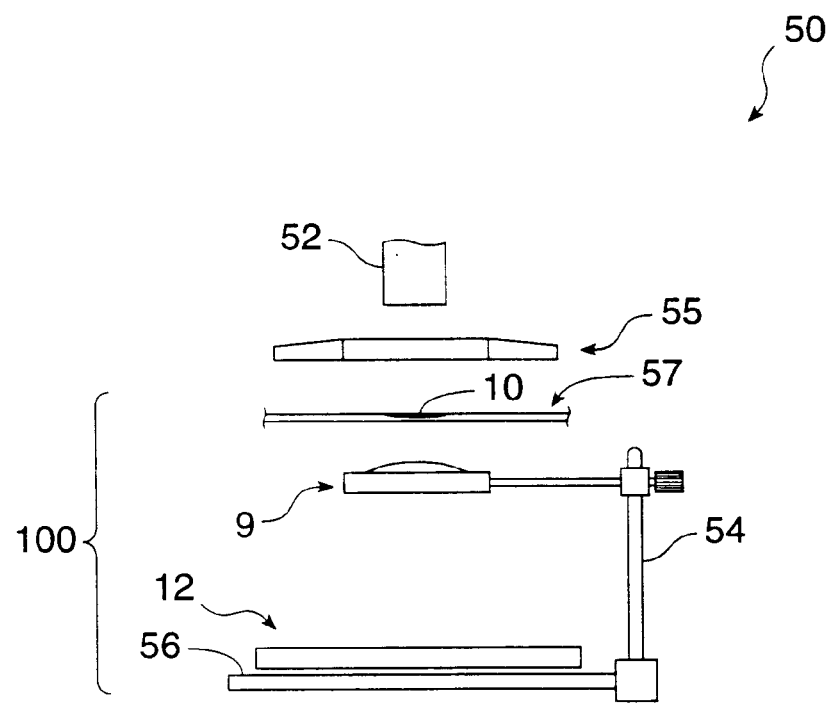
FIG. 2A is a schematic illustration of a calibration system utilizing an operating microscope.
Figure 2C:
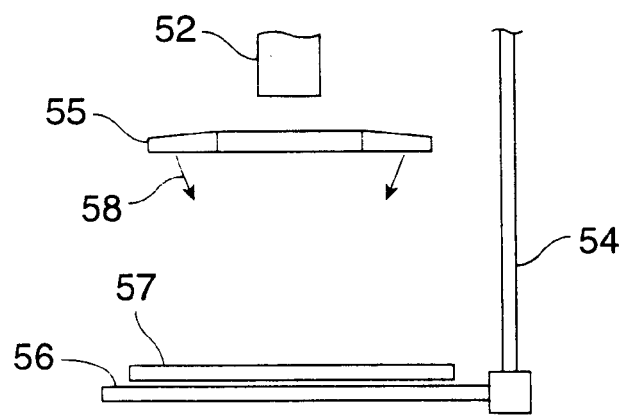
FIG. 2C is a schematic illustration of a calibration card positioned for ablation by a laser ablation system.

Prior to evaluating test surface 10, calibration card 57 is ablated as shown in FIG. 2C. A plastic sheet in the form of calibration card 57 is placed on supporting stage 56 at a position corresponding to the surface of the cornea, and test surface 10 (not shown) is selectively ablated to a desired shape, preferably a lens having refractive power. The calibration card is then removed from the support stage 56.

The ablated surface is then positioned in the optical train to measure this refractive power and shape to determine if the laser has ablated the surface in the desired manner. Test surface 10 and reference structure 12 are illuminated as discussed above, and the resulting geometrical pattern is imaged onto photodetector 20. Preferably, the reflector element 12 will include a peripheral portion (not shown) that is disposed around the ablated test surface 10 and an inner portion that is substantially aligned with the test surface in the optical axis of the system. The peripheral portion is not refracted by the test surface lens and is used to register the inner refracted portion.

To determine the refractive power of the test surface, the ratio of spacing between the geometric elements in the peripheral portion of reference structure 12 is compared with the spacing between the geometric elements in the inner portion that is refracted by the lens. Alternatively, a desired spacing of the reference structure 12 may be known for the calibration system 2. For example, the unrefracted spacing may already be programmed into the computer 26. This pre-programming permits determination of the refractive power of the test surface by evaluating a particular area of interest, such as a central optical zone without requiring evaluation of a peripheral portion. In addition, the contour of the lens can be measured by determining a relative direction of the spaced geometric elements. In other words, where line segments are known to be parallel on the reference structure, the angles between line segments (as they appear in resulting pattern 14) can be used to calculate variations in the refractive power distribution across test surface 10. If desired, the known optical properties of the ablated test surface may be used to adjust the laser ablation system by varying treatment parameters such as laser pulse intensity and exposure time.

Optical train 8 may include a known calibration card viewer 100, which can be integrated into an existing laser surgery system to create calibration system 2. Additional components such as an appropriate light detector 20, frame grabber 24 and computer 26 may be added as necessary.

One embodiment of the optical train of the present invention which utilizes an operating microscope is shown in FIG. 2A. This schematic/prototype calibration system 50 makes use of a microscope 52 of the laser ablation system. A swing arm 54 provides a stage 56 under the microscope at a position corresponding to the surface of the cornea. Lens 9 is positioned adjacent to test surface 10, and may optionally be positioned above or below test surface 10. A reference structure 12 is supported by stage 56 and illuminated by illumination source 55. Reference structure 12 is viewed through microscope 52, calibration card 57 and lens 9.

Figure 2B:
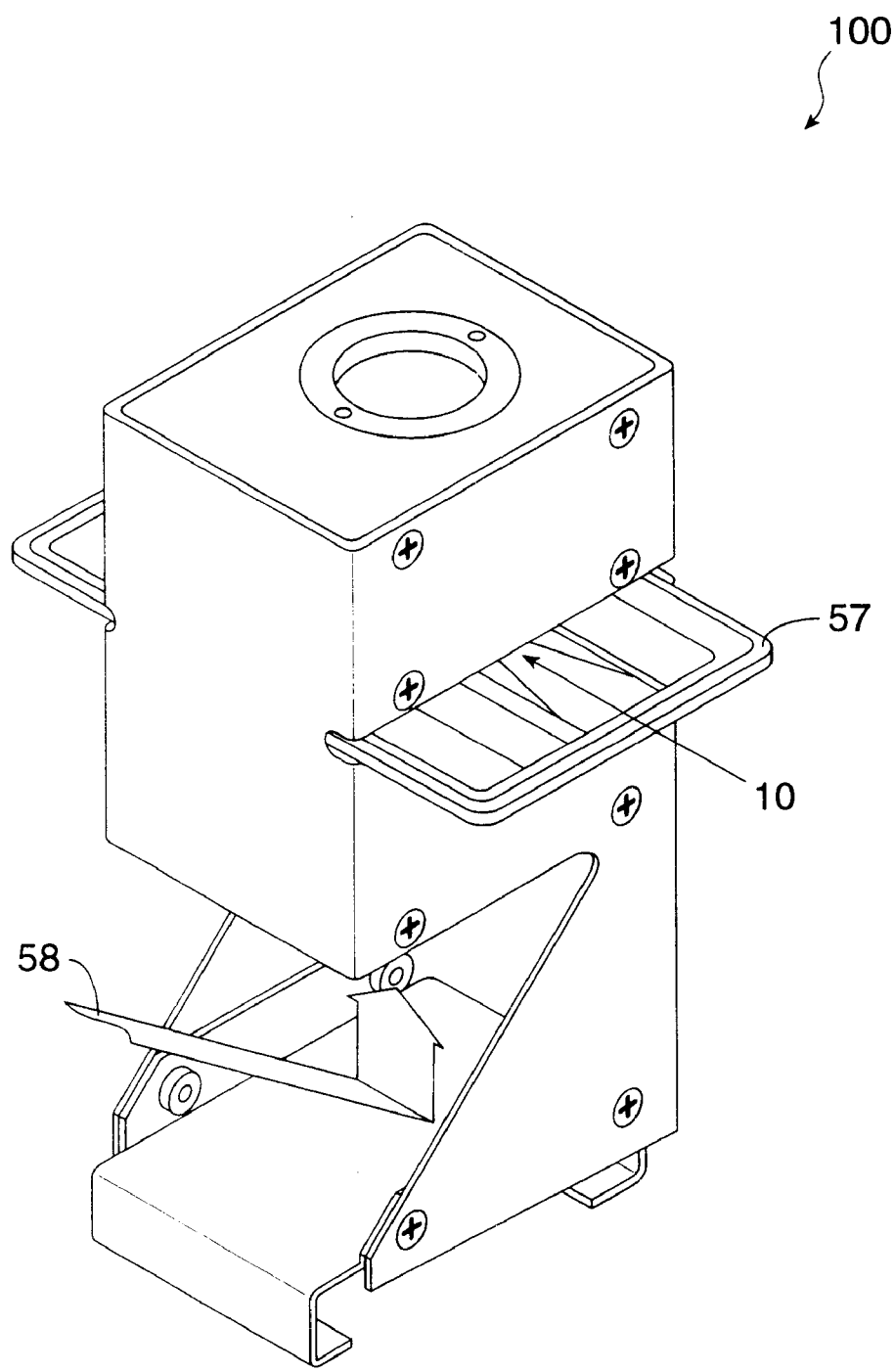
FIG. 2B is a perspective view of a calibration card viewer used in an exemplary embodiment of the calibration system shown in FIG. 2A.

Calibration system 50 preferably makes use of calibration card viewer 100 illustrated in FIG. 2B. In this embodiment, the lens and reference structure 12 are integrated into a card viewer module 100 which positions the card relative to stage 56. Card viewer 100 contains a slot for receiving calibration card 57. During the ablation process, viewer 100 is removed from stage 56 while test surface 10 of calibration card 57 is ablated. By attaching the calibration card viewer 100 to stage 56, the calibration card viewer allows the user to view the test surface 10 through microscope 52. The refractive power and shape of test surface 10 may be measured manually by viewing the ablated lens over a grid or other geometric pattern so as to determine the quality, and optionally the refractive power and shape (i.e., diameter) of the ablated plastic. Test surface quality generally indicates the overall system performance, and can be used to determine if the laser system has unacceptable internal optics, poor alignment, poor laser fluence or the like.

In an exemplary embodiment of a method for using system 50, the quality of the laser system is measured by providing a flat ablation onto the test plastic or calibration card. Flat ablations should generally have little or no optical power, should be uniform and symmetrical across the bottom, and should demonstrate a definitive transition of limited width at the edge of the ablation (typically between about 250 and 750 microns). If the test plastic has refractive power from a flat ablation, this generally indicates undesirable system performance. Conveniently, light 58 for viewing the test surface may be supplied by an illumination source of the laser system, such as by the oblique lights of the laser system (not shown) which are normally used to illuminate the cornea during a laser ablation procedure, as shown in FIG. 2B.

Figure 2D:
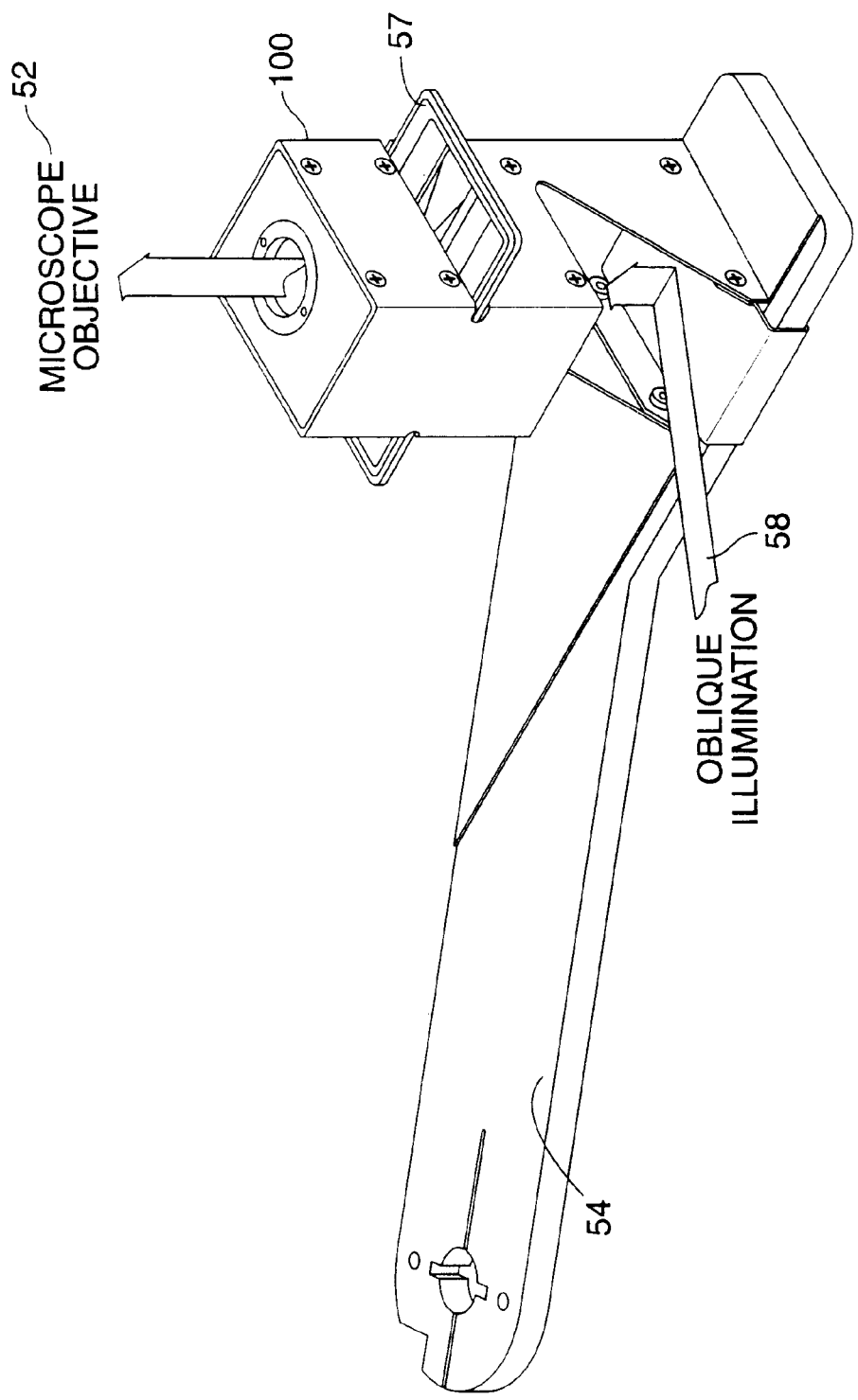
FIG. 2D is a perspective view of the calibration card viewed of FIG. 2B mounted to a swing-away arm.
Figure 3:
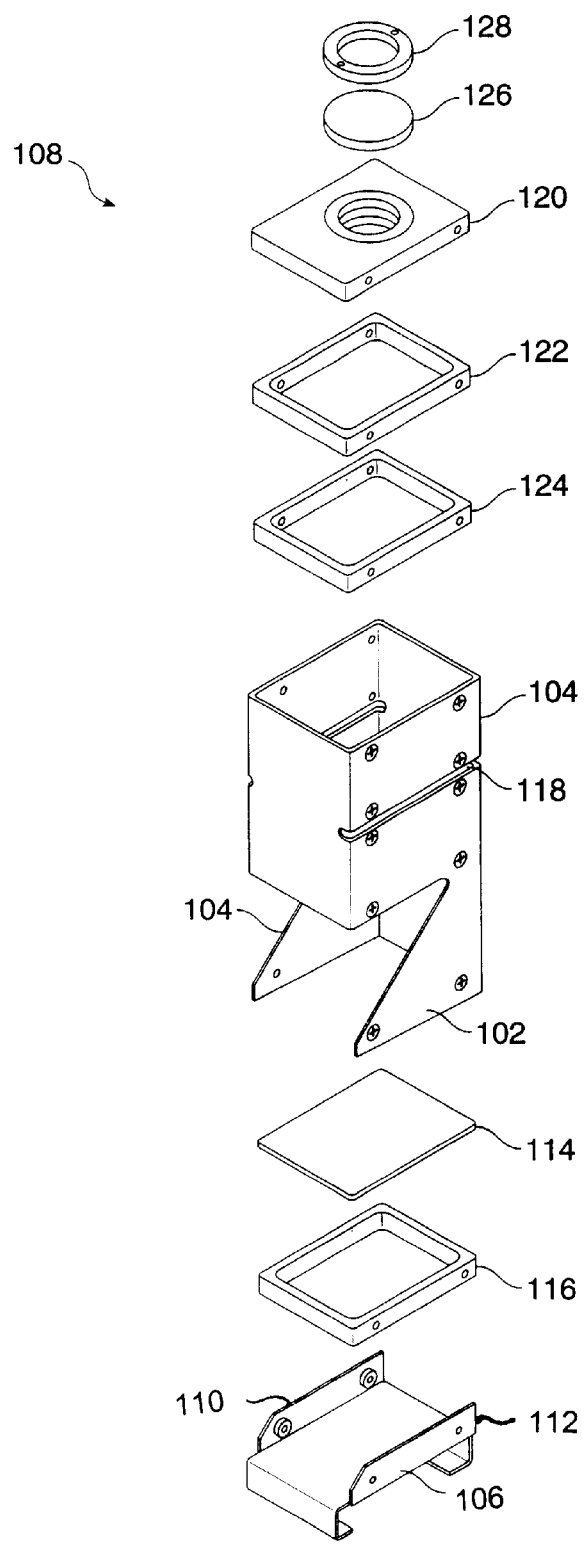
FIG. 3 is an exploded view of the calibration card viewer of FIG. 2B.
Figure 4:
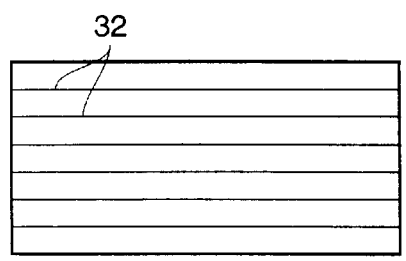
FIGS. 4 and 5 are enlarged views of patterned elements having parallel lines and a grid, respectively.

As shown in FIGS. 2B, 2D and 3, calibration card viewer 100 includes a mounting flange 102 which slides over the end of calibration swing arm 54 of calibration system 50 so that the viewer 100 is supported at stage 56 under microscope 52. Viewer 100 further includes a tubular support 104 for holding a reflector support 106 and a lens support system 108. Reflector support 106 is mounted to the bottom of tubular support 104, and includes a pair of retaining walls 110, 112 for holding a reflector grid 114 therein. Reflector grid 114 is preferably mounted within a plastic support plate 116 which is fit into the recess between the retaining walls 110, 112 of reflector support 106. Tubular support 104 further includes a slot 118 for receiving a calibration card or plastic ablation sheet 57 to be ablated by the laser and observed through microscope 52.

Lens support system 108 includes an optics mounting plate 120 and a pair of support plates 122, 124 for holding optics mounting plate 120 to tubular support 104. Optics mounting plate 120 includes a hole for receiving a lens 126, which is mounted to plate 120 with an annular retaining ring 128. Lens 126 is preferably a plano-convex glass lens for controlling the focus of the grid 114 by correcting for the limited depth of field of microscope 52. The subsequent images of the grid viewed through the ablated and non-ablated portions of the test surface appear in focus and are formed adjacent the corneal ablation plane when viewed through microscope 52. Microscope 52 preferably contains an aperture for changing the depth of field between surgery and test surface calibration.

FIGS. 8–10 are drawings representing images formed by test surface 10 and grid 114 that would be seen with the systems and methods of the present invention. Referring to FIG. 8A, grid 114 includes a peripheral portion 140 for registering an inner portion 142 that is aligned with test surface 10 of calibration card 57. FIGS. 8B and 8C illustrate "good" quality ablations for an intended flat ablation surface as the lines in the peripheral portion 140 and the inner portion 142 of grid 114 are substantially aligned with each other. FIGS. 8D and 8E illustrate "bad" quality ablations as the lines in the peripheral and inner portions 140, 142 are not aligned with each other. Thus, in the "bad" quality ablations, the supposed flat ablation of card 57 resulted in refractive power that has caused the lines in grid 114 to bend or distort. Therefore, the laser ablation system did not perform a sufficiently flat ablation, which indicates undesirable system performance, such as a bad internal optic, poor optic alignment or undesired laser fluence, etc. The digitized images may be measured to quantify the distortion based on distances between grid elements, how far a line deviates from its nominal position, and the like.

Figure 9A:
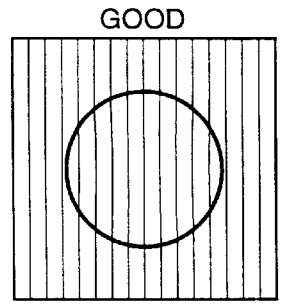
Figure 9B:
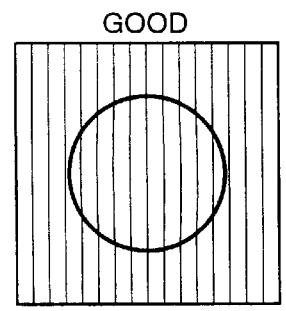
Figure 9C:
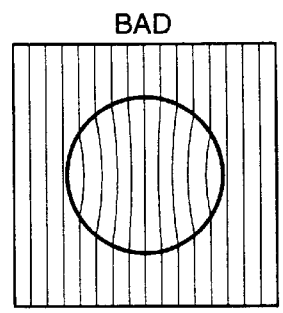
Figure 9D:
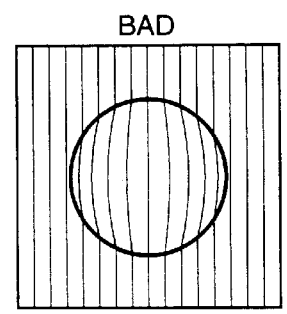
Figure 10A:
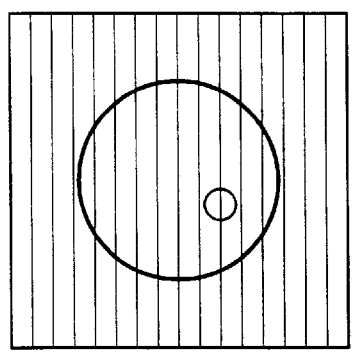
Figure 10B:
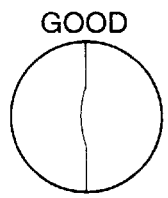
Figure 10C:
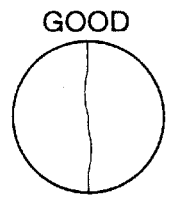
Figure 10D:
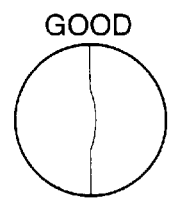
Figure 10E:
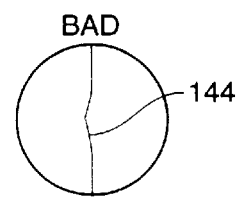

FIGS. 9A–9D, and 10A–10E further illustrate intended flat ablations, with the emphasis on the interior of the calibration card 57. In particular, FIGS. 9A and 9B illustrate "good" quality ablations because the lines of grid 114 are substantially straight with approximately equal spacing therebetween, indicating little to no optical power in card 57. FIGS. 9C and 9D illustrate "bad" quality ablations because the lines of grid 114 have widely varying spacing therebetween, which indicates that card 57 has a finite amount of refractive power. Thus, the laser system has not provided a sufficiently flat ablation onto card 57. FIGS. 10B–10E are magnified images of a portion of the image in FIG. 10A as seen through the microscope. FIGS. 10B–10D illustrate "good" quality ablations because the flaws in the lines are relatively minimal. Almost all ablations will have some bumps or bulges in the lines, which correspond to a slightly uneven ablated surfaces. The ablation shown in FIG. 10E, however, is unacceptable because the line has a discontinuity 144 which indicates defect in the ablation which causes light to be refracted at the discontinuity. Specific discontinuity characteristics may be established for acceptable and unacceptable system performance.

Figure 11:
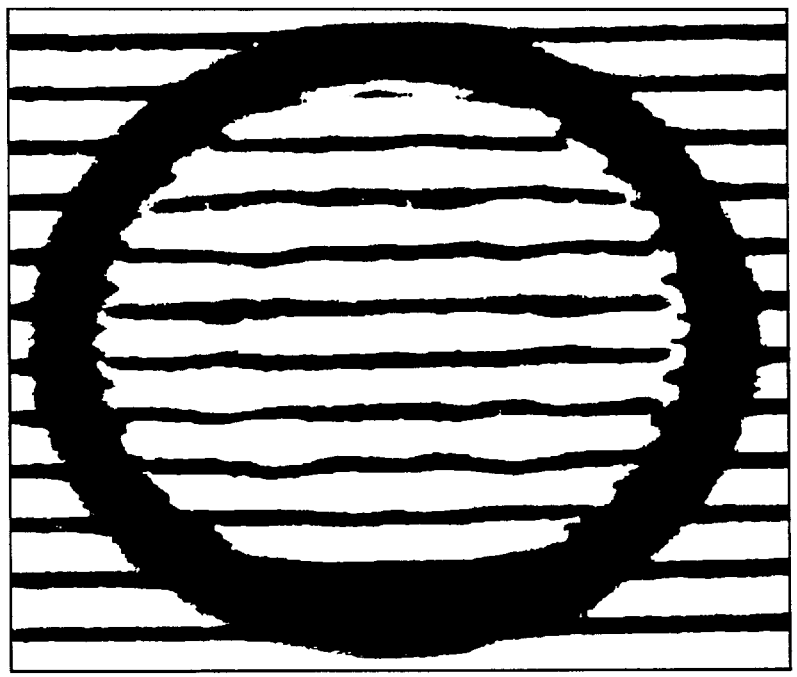
FIGS. 11–14 are exemplary images of laser test ablations, illustrating the method of measuring the quality of laser ablations with the calibration system of FIG. 2.
Figure 12:
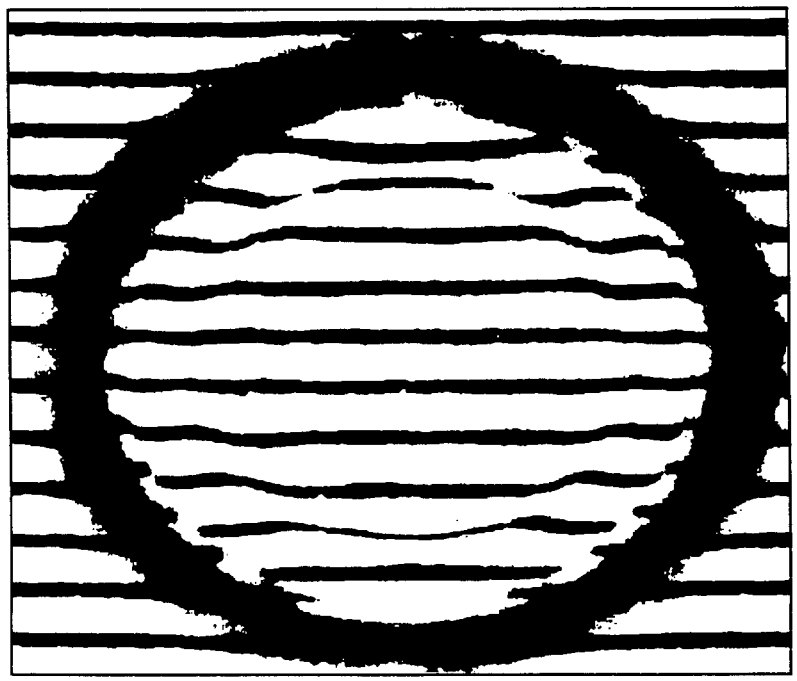
Figure 13:
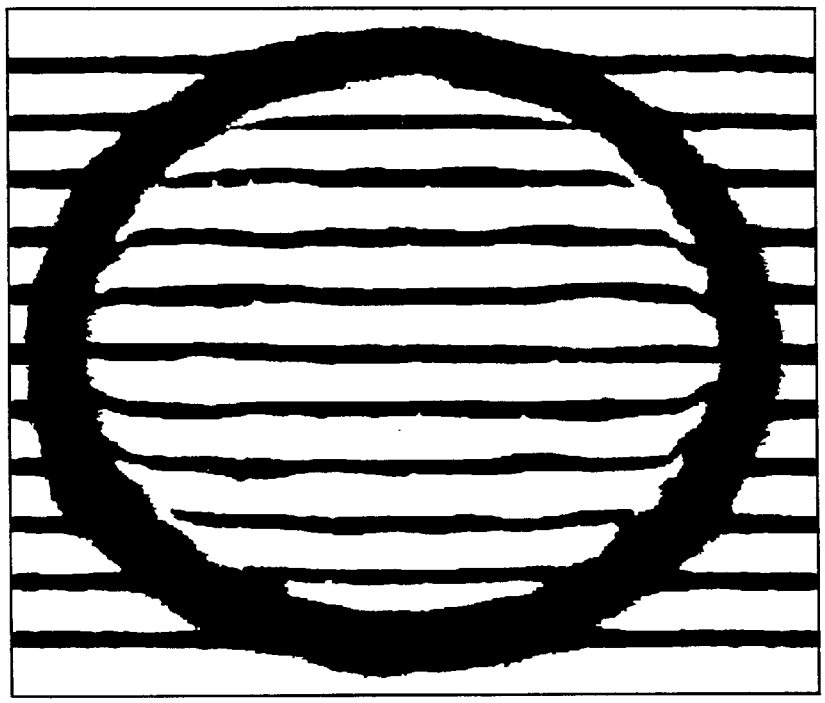
Figure 14:
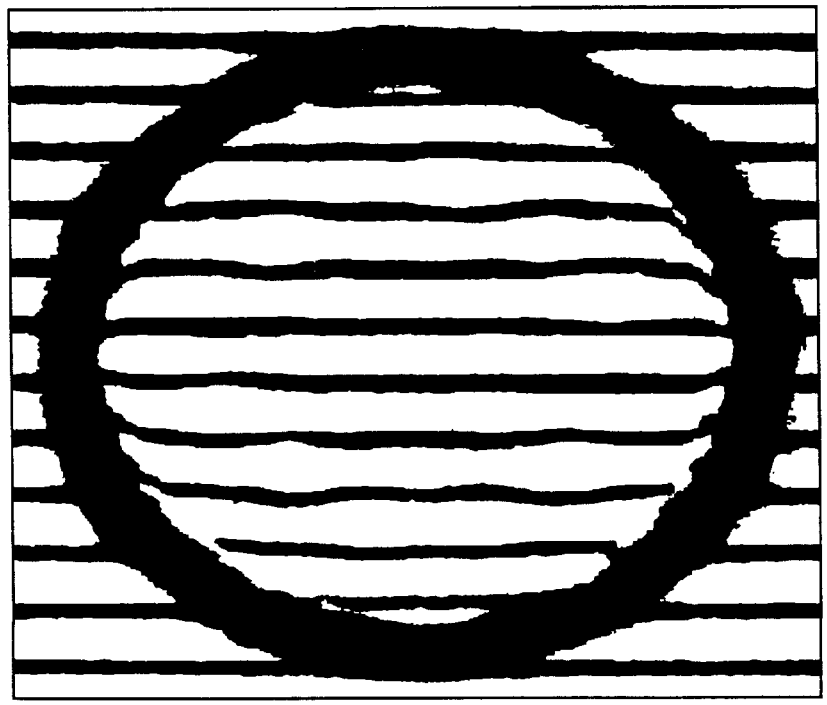

FIGS. 11–14 are examples of actual images through microscope of ablations. FIG. 11 shows a relatively "good" ablation as the lines are substantially straight, uniform and symmetric, the line spacing is substantially equal and the edge has a definite transition of limited width. FIG. 12 illustrates a measurable "cold center" which means that the center of the card 57 was underablated, causing an observable change in the optical power around the edges of the image. Cold centers could create a "central island", which is generally defined as a central area of corneal ablation that appears to be flattened less than the surrounding ablated area. A "cold center" may be caused by defective mirrors or incorrect alignment of the laser delivery system. FIG. 13 illustrates a "hot center" which means the center of the card 130 has been overablated, causing an observable change in the optical power near the center. A "hot center" may be caused by incorrect alignment of the laser delivery system. Finally, FIG. 14 illustrates an edge that is not sharp enough, which indicates a sloped surface instead of a steep wall at the edge of the ablation. A sloped surface at the edge of an ablation may be corrected by improving the imaging of the aperture defining the edge of the ablation.

Analysis of the ablation may be automated using the systems described herein above. In some embodiments, the computer may indicate whether the ablation system is sufficiently accurately calibrated to perform any ablation, or to perform a particular photorefractive resculpting. The computer system may optionally adjust the ablation algorithm based on the actual shape of the test ablation, either automatically or with manual input, to avoid central islands, for example. Hence, the system can provide a feedback mechanism to enhance the accuracy of the change in corneal shape effected by a laser.

While the present invention has been described in some detail, by say of example and for clarity of understanding, a variety of adaptations, modifications, and changes will be obvious to those of skill in the art. Therefore, the scope of the invention is limited solely by the appended claims.

What is claimed is:

1. A method for calibrating a laser ablation system, the method comprising:
   selectively ablating a test surface with the laser system;
   superimposing a geometrical test pattern and the ablated test surface to generate a resulting pattern;
   imaging the resulting pattern onto a photodetector, the photodetector comprising a charge couple device;
   digitizing at least a portion of the imaged resulting pattern by generating electrical signals with the photodetector in response to the imaged resulting pattern; and,
   analyzing the digitized pattern by processing the electrical signals with a computer to determine the ablation characteristics of the laser ablation system.

2. A method for calibrating a laser ablation system, the method comprising:
   selectively ablating a test surface with the laser system;
   superimposing a geometrical test pattern and the ablated test surface to generate a resulting pattern;
   imaging the resulting pattern onto a photodetector;
   digitizing at least a portion of the imaged resulting pattern by generating electrical signals with the photodetector in response to the imaged resulting pattern and directing the electrical signals to a frame grabber which produces a time sequence series of electrical signals representative of the imaged resulting pattern; and,
   analyzing the digitized pattern by processing the electrical signals with a computer to determine the ablation characteristics of the laser ablation system.

3. A method for calibrating a laser ablation system, the method comprising:
   selectively ablating a test surface with the laser system;
   superimposing a geometrical test pattern and the ablated test surface to generate a resulting pattern;
   imaging the resulting pattern onto a photodetector;
   digitizing at least a portion of the imaged resulting pattern by generating electrical signals with the photodetector in response to the imaged resulting pattern;
   analyzing the digitized pattern by processing the electrical signals with a computer to determine the ablation characteristics of the laser ablation system; and,
   adjusting the laser ablation system with an automatic feedback mechanism based on the processed electrical signals.

4. A method for light projection of a test pattern for use with a laser ablation system, the laser ablation system capable of reshaping a surface with an ablative laser, the method comprising:
   illuminating a geometrical test pattern through an ablated test surface, which is aligned with the ablative laser, wherein the test pattern is disposed along a path of light between a light source and the test surface;
   imaging the illuminated test pattern through the test surface onto a photodetector;
   digitizing and analyzing the image; and,
   adjusting the ablative laser with a feedback mechanism based on the digitized and analyzed image.

5. The method of claim 4, wherein the geometrical test pattern comprises a grid of regularly spaced lines.

6. The method of claim 4, wherein the illumination step is carried out by projecting light from the light source toward the test pattern and the test surface.

7. The method of claim 6, wherein the geometrical test pattern has an inner portion aligned with the test surface and a peripheral portion disposed beyond the ablated test surface such that the light passing through the peripheral portion from the geometrical test pattern is not redirected by the test surface.

8. The system of claim 7, wherein the geometrical pattern comprises regularly spaced lines, and further comprising determining spacing ratios between the spaced lines in the peripheral and inner portions to determine a distribution of refractive power of the test surface.

9. The system of claim 7, further comprising measuring a contour of the test surface by determining a continuity of an element of the geometric pattern which extends between the peripheral and inner portions.

10. The method of claim 4, wherein the digitizing and analyzing step is carried out by transforming the light with the photodetector into electrical signals and processing the electrical signals so that the laser can be adjusted based on said electrical signals.

11. The method of claim 3, wherein the superimposing step comprises reflecting light off a partially reflective reference structure.

12. The method of claim 3, wherein the analyzing step comprises determining a quality of the ablated test surface.

13. The method of claim 3, wherein the test surface is ablated into a lens, the analyzing step comprising determining a refractive power of the lens.

14. The method of claim 3, wherein the superimposing step comprises projecting a peripheral portion of the geometric pattern through a test material surface around the ablated test surface and projecting an inner portion of the geometric pattern through the ablated test surface, and wherein the analyzing step comprises comparing elements of the geometrical pattern from the peripheral portion and the inner portion of the resulting geometrical pattern.

15. The method of claim 14, wherein the geometrical pattern comprises regularly spaced elements, and further comprising determining a ratio of spacing between the spaced elements in the peripheral and inner portions of the resulting pattern to determine a distribution of refractive power along the test surface.

16. The method of claim 14, further comprising verifying a contour of the test surface adjacent a test surface edge by measuring a continuity of an element of the resulting geometric pattern which extends between the inner portion and the outer portion.

17. The method of claim 3, wherein the laser ablation system is adjusted based on at least one of refractive power, quality, and shape of the test surface determined during the analyzing step.

18. The method of claim 3, wherein the selectively ablating step comprises applying laser energy to the test surface to approximate at least one procedure selected from the group consisting of astimagtic correction of a human eye, myopic correction of a human eye, and hyperopic correction of a human eye.

* * * * *